United States Patent

Tung

[11] Patent Number: 5,868,715
[45] Date of Patent: Feb. 9, 1999

[54] INTRAVENOUS METERING DEVICE HAVING AUTOMATIC STOPPER

[76] Inventor: Chen Chang Tung, P.O. BOX 63-150, Taichung, Taiwan

[21] Appl. No.: 969,757

[22] Filed: Nov. 13, 1997

[51] Int. Cl.$^6$ ..................................................... A61M 5/00
[52] U.S. Cl. ........................... 604/256; 604/247; 604/245; 604/254
[58] Field of Search ................................. 604/247, 30, 31, 604/32, 33, 245, 249, 251, 254, 255, 256; 137/409

[56] References Cited

U.S. PATENT DOCUMENTS

| | | | |
|---|---|---|---|
| 3,227,173 | 1/1966 | Bernstein | 604/254 |
| 4,947,154 | 8/1990 | Hwang | 604/254 X |
| 5,415,325 | 5/1995 | Shu | 604/254 X |
| 5,722,961 | 3/1998 | Fan | 604/254 |

Primary Examiner—Wynn Wood Coggins
Assistant Examiner—N. Kent Gring

[57] ABSTRACT

An intravenous metering device having automatic stopper comprises a connecting tube that can be inserted into a liquid bottle at one end such that a fluid communication therebetween can be establish. The transfusion tube being connected to a liquid barrel that has a relative larger diameter and is adjacent to the liquid bottle. The liquid barrel serves a buffering device in which the liquid from the bottle is firstly and temporary stored thereof. The second end of the transfusion tube is connected with a catheter that can be punctured into the vein of patient. A regulating device being enveloped onto the transfusion tube at suitable position. Characterized in that the junction between the lower end of the liquid barrel and the upper end of the transfusion tube is formed with a cone-shape recess in which a valve that can be axially engaged thereof is disposed. The valve is floated over the liquid surface of the liquid barrel. The lower end of the valve is provided with a cone-shape stopper. Wherein when the liquid level within the liquid barrel becomes lower and lower, the stopper of the valve may be completely seated and engaged within the cone-shape recess to block the liquid flow.

1 Claim, 4 Drawing Sheets

INTRAVENOUS METERING DEVICE HAVING AUTOMATIC STOPPER

FIELD OF THE INVENTION

The present invention relates to a metering device, more particularly, to an intravenous metering device that has an automatic stopper therein.

DESCRIPTION OF PRIOR ART

Intravenous injection is a dispensable measurement in directing liquid, such as saline, medicine or even blood into the vein of patient, especially in a critical condition.

As shown in FIG. 1, the conventional metering device generally comprises a transfusion tube 1 that is in fluid communication of a liquid bottle when one end of the transfusion tube 1 is punctured into the bottle. The second end 1A of the transfusion tube 1 is provided with a catheter in which a needle 2 is mounted for puncturing into the vein of patient. The upper portion 1B of the transfusion tube 1 is further provided with a liquid barrel 3 in which a certain amount of liquid is stored temporary therein. The liquid within the liquid barrel is supplied by the liquid drops from the bottle and the number of liquid drops per minute can be controlled by a regulating device 5 that includes a roller 5A rolling along an inclined surface.

When the liquid from the bottle is exhausted, the roller 5A is moved to the lowest position to squeeze the transfusion tube 1 such that the liquid flow can be completely blocked. However, this shall be done manually by either the nurse or watcher. However, if the transfusion tube 1 is not blocked in time, the air from the bottle will be directed into the vein via the transfusion tube 1. This is very dangerous to the patient if excess air is directed into the vein. Accordingly, when the patient is receiving a IV, the watcher or nurse shall be alert to the remained amount of the liquid bottle.

Even there advanced monitoring device for IV, it is too expensive and not all the patient can afford it. In light of this, there is a need to provide a safe metering device for IV and this is also affordable by all the patient.

SUMMARY OF THE INVENTION

It is the objective of this invention to provide an intravenous metering device having automatic stopper. By providing a valve that floats over the surface of a liquid barrel, the transfusion tube can be readily blocked when the liquid within the liquid barrel is lowered to a lower limit. In light of this, the potential danger of directing air into the vein can be therefore prevented.

In order to achieve the object set forth, an intravenous metering device having automatic stopper is provided. The metering device comprises a connecting tube that can be inserted into a liquid bottle at one end such that a fluid communication therebetween can be establish. The transfusion tube being connected to a liquid barrel that has a relative larger diameter and is adjacent to the liquid bottle. The liquid barrel serves a buffering device in which the liquid from the bottle is firstly and temporary stored thereof. The second end of the transfusion tube is connected with a catheter that can be punctured into the vein of patient. A regulating device being enveloped onto the transfusion tube at suitable position. Characterized in that the junction between the lower end of the liquid barrel and the upper end of the transfusion tube is formed with a cone-shape recess in which a valve that can be axially engaged thereof is disposed. The valve is floated over the liquid surface of the liquid barrel. The lower end of the valve is provided with a cone-shape stopper. Wherein when the liquid level within the liquid barrel becomes lower and lower, the stopper of the valve may be completely seated and engaged within the cone-shape recess to block the liquid flow.

BRIEF DESCRIPTION OF DRAWINGS

In order that the present invention may more readily be understood the following description is given, merely by way of example with reference to the accompanying drawings, in which.

DETAILED DESCRIPTION OF PREFERRED EMBODIMENT

Figure 1:
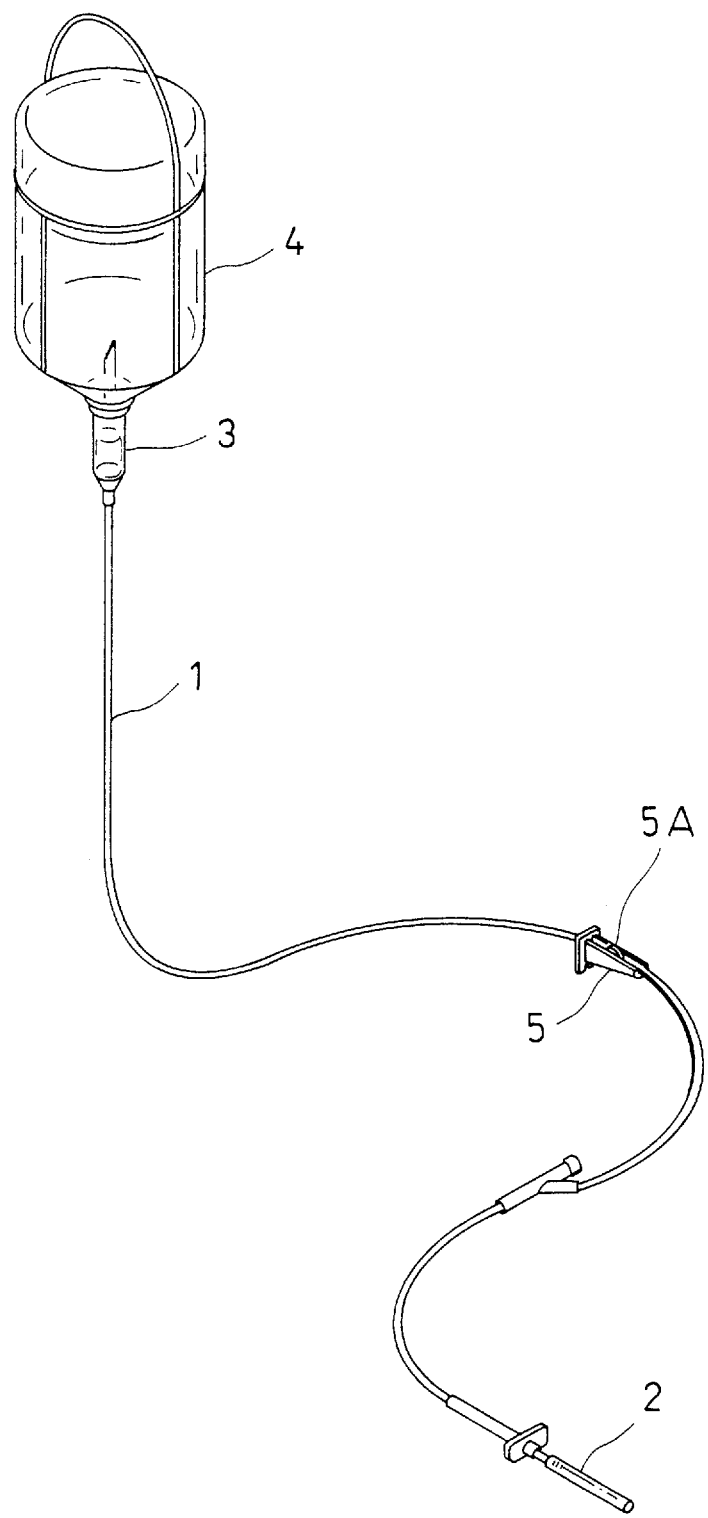
FIG. 1 is a perspective view of the conventional metering device.
Figure 2:
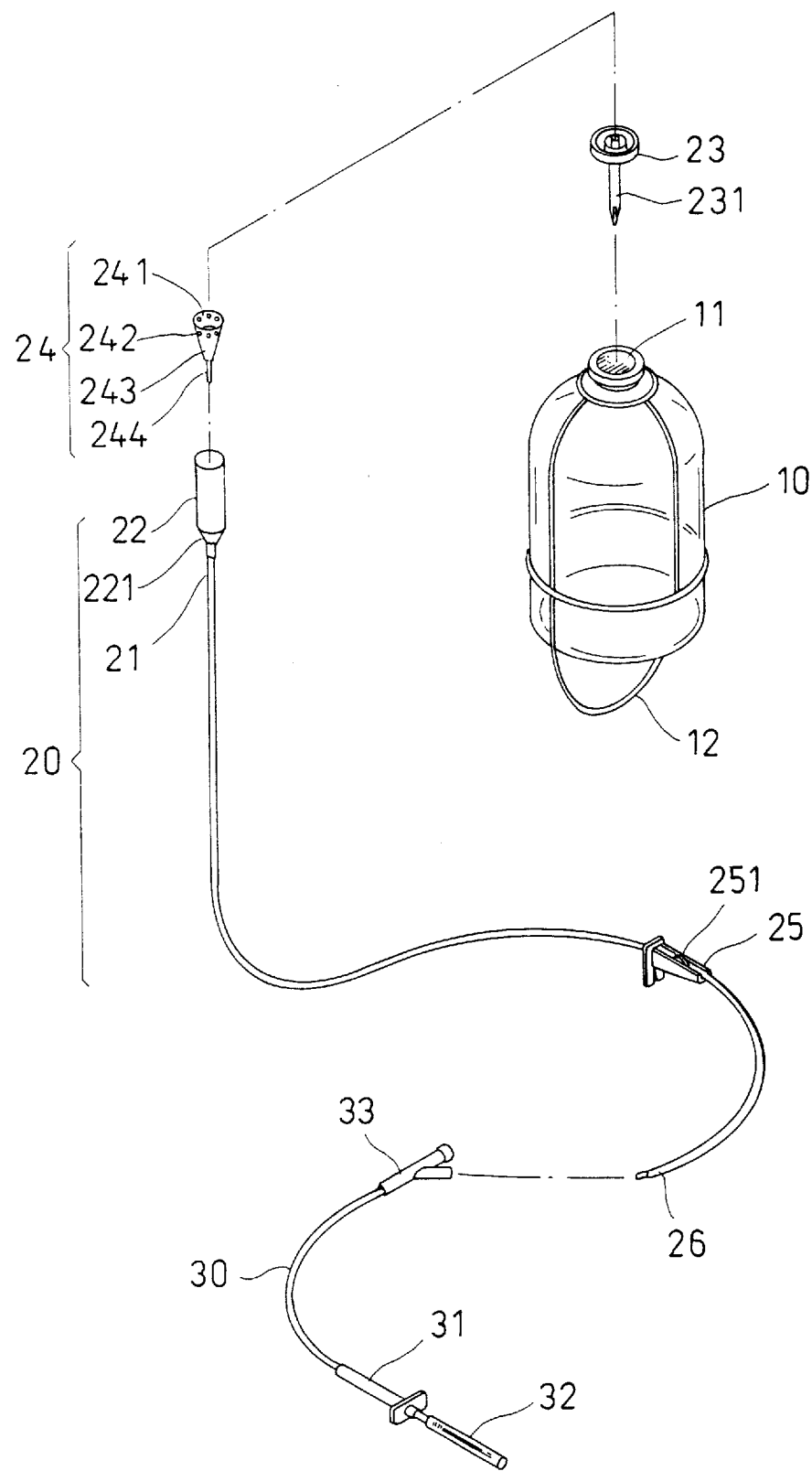
FIG. 2 is an exploded perspective view of the metering device made according to the present invention.

Referring to FIG. 2, the metering device for intravenous injection generally comprises a liquid bottle 10, a transfusion hose 20, and a catheter 30.

The liquid bottle 10 is known to the skilled in the art and it generally contains a saline or dextrose liquid. The opening 11 of the bottle 10 is sealed with aluminum foil and a vacuum condition is established within the bottle 10. The lower end of the bottle 10 is provided with a hanging band 12 that can be readily hanged onto hooker when it is to meter.

The transfusion tube 20 is a clear tube and one end of the tube 20 is connected to a liquid barrel 22 that has a relative larger diameter. The liquid barrel 22 is further provided with an enclosing lid 23 at top. The enclosing lid 23 is provided with a connector 231 that is directed upward. The connector 231 can be pieced through the aluminum foil on the opening 11 of the bottle 10 such that a fluid communication between the liquid barrel 22 and the bottle 10 is established. The liquid barrel 22 serves as a buffering device in which the liquid from the bottle 10 is firstly and temporary stored thereof, and then is further metered to the vein through the transfusion tube 20. A cone-shape cavity 221 is formed between the lower end of the storing barrel 22 and the upper end of the transfusion tube 20. The liquid barrel 22 is pivotally mounted with a valve 24. The valve 24 is made from toxicity-free material and the specific gravity of it is about 0.93. By this arrangement, the valve 24 normally floats on the surface of the liquid that is within the cone-shape cavity 221. The valve 24 is further defined with a cup-shape recess 241 at top and the peripheral of the recess 241 is provided with a ring of orifices 242 and which are located at a certain height. By this arrangement, when the liquid exceeds the orifices 242, it may drain off. The bottom of the valve 24 is terminated with a stopper 243 having a cone-shape and which can be complimentary matched with the coneshape recess 221 at the bottom of the liquid barrel 22, as clearly shown in FIG. 3. When the stopper 243 is engaged with the recess 221, the liquid flow can be completely blocked. In order to provide a stable ascending and descending movement axially, a guiding stick 244 is extended from the stopper 243. The transfusion tube 20 is further provided with a regulating device 25 that is provided with a roller 251 that can be moved along an inclined surface. With the upward and downward movement of the roller 251 along the inclined surface, the inner diameter of the transfusion tube 20 can be readily controlled. As a result, the drops per minute can be readily adjusted through the regulating device 25. This regulating device 25 is known to the skilled in the art and no detailed description is given. The second end of the transfusion tube 20 is terminated to a coupler 26.

Referring to FIG. 2, the catheter 30 is made from the material similar to the transfusion tube 20. One end of the catheter 30 is fixedly attached with a needle 32 that can be punctured through the skin and into the vein below the skin. The other end is provided with a hub 33 that can be engaged with the coupler 26 of the transfusion tube 20.

Figure 3:
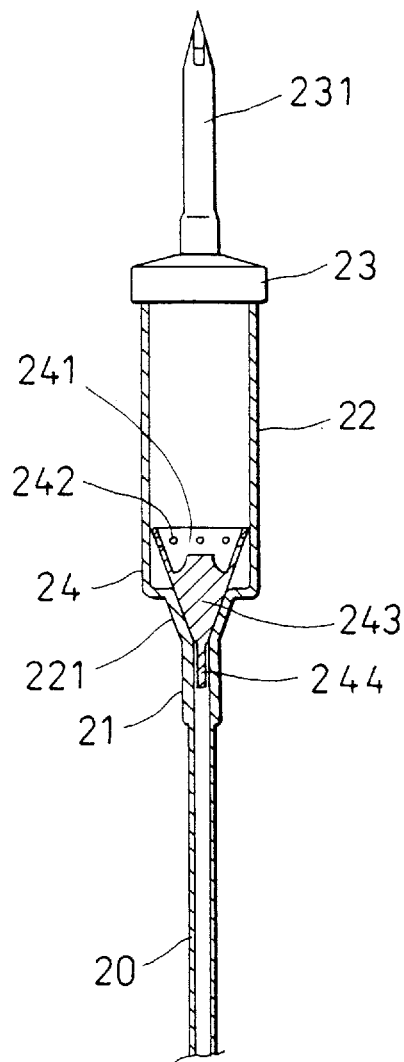
FIG. 3 is a partial, enlarged cross sectional view of the metering device made according to the present invention.
Figure 5:
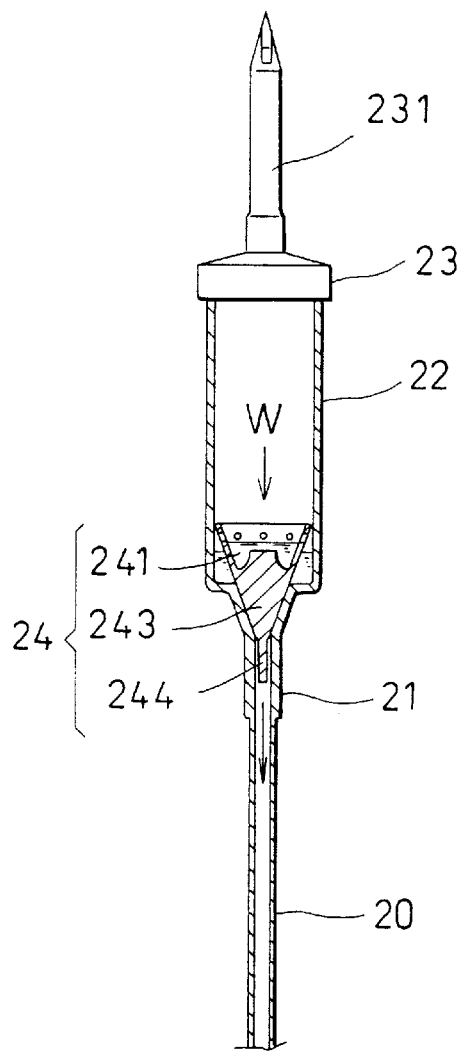
FIG. 5 is a schematic illustration showing the transfusion of the liquid is stopped by the metering device.

The relationship between the liquid barrel 22, the enclosing lid 23 and the valve 24 will be detailedly described as referred to FIG. 3.

Figure 4:
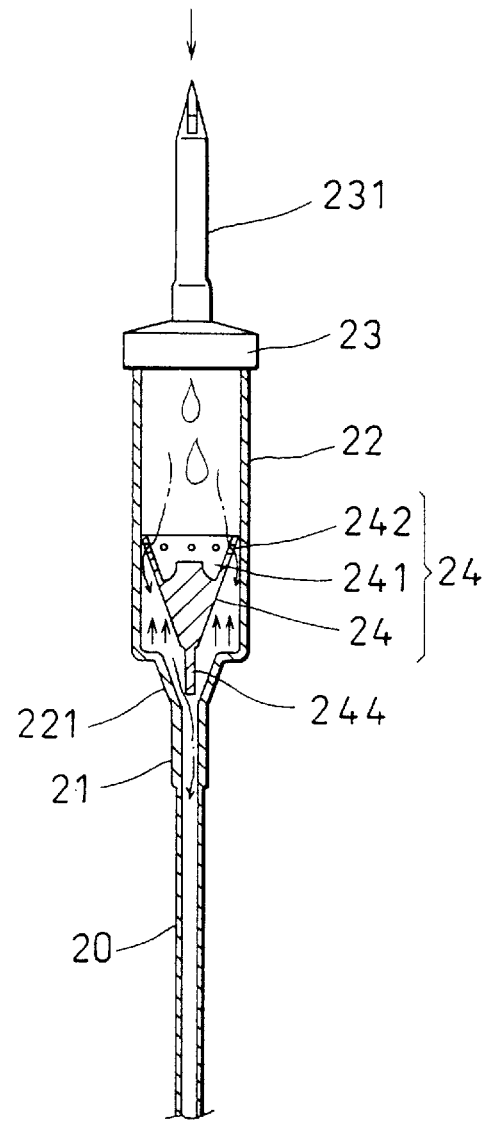
FIG. 4 is a schematic illustration showing the transfusion of the liquid is commenced by the metering device.

The connector 231 is firstly punctured through the aluminum foil on the opening 11 of the bottle 10 and then establish a fluid communication between the bottle 10 and the transfusion tube 20. Then the bottle 10 is hanged onto a mounting hooker and the liquid contained therein can be metered, as shown in FIG. 4. In the beginning, the liquid is drained out from the needle 32 to expel the air therein. However, a suitable of liquid is suitably remained within the liquid barrel 22 such that the valve 24 is lifted to a certain height by the float of the liquid. Normally, the height of the liquid, i.e. the level of the liquid, is dependent to the drops per minute. As the recess 241 of the valve 24 is provided with a ring of orifices 242, the liquid over the orifices 242 will automatically drain out and flow into the little pond within the liquid barrel 22. As the liquid drops are constantly supplied from the liquid bottle 10, the valve 24 can be kept in the given height.

Because the valve 24 is lifted over the surface of the liquid pond within the liquid barrel 22, the stopper 243 at the lower end of the valve 24 will be disengaged from the cone-shape recess 221. As a result, the liquid can be constantly directed into the vein in a controlled flow rate. The flow rate can be controlled through the regulating device 25 that is known to the skilled in the art. Through the adjustment of the regulating device 25, the liquid drops per minute can be readily controlled, as clearly shown in FIG. 2.

After the liquid with the liquid bottle 10 is exhausted, the liquid barrel 22 will not be supplied with liquid drops any more while it is still deviated. As the liquid level within the liquid pond of the liquid barrel 22 becomes lower and lower, the valve 24 is lowered as the level is decreased. Since the cup-shape recess 241 of the valve 24 is still contained with a certain amount of liquid, the valve 24 will be moved downward and the downward movement will be beneficially guided by the guiding stick 244.

When the liquid within the cone-shape recess 221 of the liquid barrel 22 becomes lower and lower, the stopper 243 will contact with the cone-shape recess 221 of the liquid barrel 22. As the transfusion tube 20 has a certain length between the liquid barrel 22 and the catheter 30, the remained liquid within the transfusion tube 20 will generate a downward sucking force at the front end 21. This sucking force together with the total weight w within the cup-shape recess 221 of the valve 24 will cause the valve 24 be quickly seated into the cone-shape recess 221. In this event, the cone-shape recess 221 will be sealed by the cone-shape stopper 243. When the cone-shape recess 221 is sealed by the cone-shape stopper 243, there is still some of the liquid remained at the lower portion of the liquid barrel 22, accordingly, an air-tight engagement between the stopper 243 and the recess 221 will be established thereof. In this case, the transfusion tube 20 is completely sealed by the valve 24 and the air within the liquid bottle 10 will not flow into the transfusion tube 20. Furthermore, the sucking force generated by the remained liquid within the transfusion tube 20 will cause the stopper 243 be tightly seated within the recess 221 and the intravenous injection can be completely stopped. The safety of the patient who receives the IV can be ensured. Even the nurse, family members are not at site, the transfusion tube 20 of the IV can be automatically stopped by the valve 24 located within the liquid barrel 22. It can be readily appreciated that no negative effect or damage will be imposed to the patient. By the provision of the metering device suggested by the present invention, the laborious work and metal pressure of the nursery can be softened and the medical quality can be therefore upgraded.

On the other hand, the valve 24 and the liquid barrel 22 feature a simple and compact configuration that can be readily manufactured in a comparatively low cost. With this feature, the IV can be conducted at a more safe and convenient environment. This is really a good new to the patient and the medical person.

I claim:

1. An intravenous metering device having an automatic stopper, said intravenous metering device comprising a connection tube, a liquid bottle in communication with said connection tube, and a transfusion tube connected with a liquid barrel that has a relatively larger diameter and is adjacent to said liquid bottle, said liquid barrel serving as a buffering device in which the liquid from said bottle is first and temporarily stored, a second end of said transfusion tube being connected with a catheter that can be punctured into the vein of a patient, a regulating device being enveloped onto said transfusion tube at a suitable position for controlling the flow rate of the liquid, characterized in that a junction between a lower end of said liquid barrel and an upper end of said transfusion tube is formed with a cone-shape recess that is shaped to receive a valve, and a valve being axially engageable therewith, said valve being floated over a liquid surface of said liquid barrel such that a lower end of said valve is provided with a cone-shape stopper, and that said stopper of said valve can be completely seated and engaged within said cone-shape recess to block the liquid flow at the time when the liquid level within said liquid barrel is lowered, said valve having an outer diameter which is complimentarily matched with an inner diameter of said cone-shape recess, said valve further having a cup-shape recess for containing a certain amount of liquid, said valve being guided into said cone-shape recess by a guiding stick;

wherein said cup-shape recess is provided with a ring of orifices to drain the liquid out of said cup-shape recess.

* * * * *